(12) United States Patent
Denson et al.

(10) Patent No.: US 9,995,752 B2
(45) Date of Patent: Jun. 12, 2018

(54) METHODS AND COMPOSITIONS FOR DETERMINING AND TREATING RELAPSE IN INFLAMMATORY BOWEL DISEASE

(71) Applicants: CHILDREN'S HOSPITAL MEDICAL CENTER, Cincinnati, OH (US); Westfaelische Wilhelms-Universitaet Muenster, Muenster (DE)

(72) Inventors: Lee A. Denson, Wyoming, OH (US); Bruce C. Trapnell, Liberty Township, OH (US); Jan Däbritz, Berlin (DE)

(73) Assignees: Children's Hospital Medical Center, Cincinnati, OH (US); Westfaelische Wilhelms-Universitaet Muenster, Muenster (DE)

( * ) Notice: Subject to any disclaimer, the term of this patent is extended or adjusted under 35 U.S.C. 154(b) by 0 days. days.

(21) Appl. No.: 14/890,257

(22) PCT Filed: May 13, 2014

(86) PCT No.: PCT/US2014/037927
§ 371 (c)(1),
(2) Date: Nov. 10, 2015

(87) PCT Pub. No.: WO2014/186416
PCT Pub. Date: Nov. 20, 2014

(65) Prior Publication Data
US 2016/0084846 A1    Mar. 24, 2016

Related U.S. Application Data

(60) Provisional application No. 61/823,323, filed on May 14, 2013.

(51) Int. Cl.
*G01N 33/68* (2006.01)
*G01N 33/564* (2006.01)

(52) U.S. Cl.
CPC ....... *G01N 33/6854* (2013.01); *G01N 33/564* (2013.01); *G01N 33/6893* (2013.01); *G01N 2333/7153* (2013.01); *G01N 2800/065* (2013.01); *G01N 2800/52* (2013.01); *G01N 2800/54* (2013.01)

(58) Field of Classification Search
None
See application file for complete search history.

(56) References Cited

U.S. PATENT DOCUMENTS

| | | | | |
|---|---|---|---|---|
| 9,541,560 B2 * | 1/2017 | Denson | ............... | G01N 33/6863 |
| 2010/0035850 A1 * | 2/2010 | Karlstadt Meyeroff | ............... | G06Q 50/16 514/166 |
| 2010/0255513 A1 * | 10/2010 | Denson | ............... | G01N 33/6863 435/7.92 |

OTHER PUBLICATIONS

Pardi et al., Predicting relapse in patients with inflammatory bowel disease: what is the role of biomarkers? Gut, 54, 321-322, 2005.*
Costa et al., Calprotectin is a stronger predictive marker of relapse in ulcerative colitis than in Crohn's disease. Gut, 54, 364-368, 2005.*
Nylund et al., Granulocyte Macrophage-Colony-stimulating Factor autoantibodies and increased intestinal permeability in Crohn disease. J. Pediatr. Gastroenterol. Nutr., 52, 542-548, 2011.*
Tibble et al. (Surrogate Markers of Intestinal Inflammation Are Predictive of Relapse in Patients with Inflammatory Bowel Disease. Gastroenterol. 119, 15-22, 2000.*
Dabritz, et al, "Granulocyte macrophage colony-stimulating factor auto-antibodies and disease relapse in inflammatory bowel disease," Am J Gastroenterol, 108:1901-1910 (2013).
Gisbert, et al., "Fecal calprotectin and lactoferrin for the prediction of inflammatory bowel disease relapse," Inflam Bowel Dis., 15:1190-1198 (2009).
Musci, J.O., et al., "Utility of Surrogate Markers for the Prediction of Relapses in Inflammatory Bowel Diseases," J. Gastroenterol, 51(6):531-547 (2016).
Bao, J., Capillary electrophoretic immunoassays, J. Chromatogr. B. 699:463-480 (1997).
Bernasconi E, et al. Granulocyte-Macrophage Colony-Stimulating Factor Elicits Bone Marrow Derived Cells that promote Efficient Colonic Mucosal Healing, Inflamm Bowel Dis. 16:428-41 (2010).
Bishop and Davis, A Flow Cytometric Immunoassay for $B_2$-microglobulin in whole blood, J. Immunol. Methods 210:79-87 (1997).
Browne SK, et al., Immunodeficiency secondary to anti-cytokine autoantibodies, Curr Opin Allergy Clin Immunol 10:534-541 (2010).
Becton Dickinson Catalog No. 554502, Purified Rant Anti-Human GM-CSF (2007).
Colombel JF, et al., Infliximab, Azathioprine, or Combination Therapy for Crohn's Disease, N Engl J Med 362:1383-95 (2010).
Crandall WV, et al., Improved Outcomes in a Quality Improvement Collaborative for Pediatric Inflammatory Bowel Disease, Pediatrics 129:e1030-41 (2012).
Dabritz J, et al. Improving Relapse Prediction in Inflammatory Bowel Disease by Neutrophil-Derived S100A12, Inflamm Bowel Dis 19(6):1130-1138 (2013).
Danese, S., New therapies for inflammatory bowel disease: from the bench to the bedside, S. Gut 61:918-32 (2012).
Ding L. et al., Determination of Human Anticytokine Autoantibody Profiles Using a Particle-Based Approach, J. Clin. Immunol. 32: 238-245 (2012).
Dranoff G., Granulocyte-Macrophange Colony Stimulating Factor and Inflammatory Bowel Disease: Establishing a connection, Gastroenterology 141:28-31 (2011).

(Continued)

*Primary Examiner* — Elly-Gerald Stoica
(74) *Attorney, Agent, or Firm* — Knobbe, Martens, Olson & Bear LLP

(57) ABSTRACT

Described are methods and compositions for evaluating the relapse risk n subjects having an inflammatory bowel disease (IBD). Some embodiments include selecting a treatment for an evaluated IBD relapse risk in a subject.

18 Claims, 4 Drawing Sheets

(56) References Cited

OTHER PUBLICATIONS

Ebert EC, et al., Non-response to infliximab may be ude to innate neutralizing anti-turmor necrosis factor-a antibodies, Clin Exp Immunol 154:325-31 (2008).
Egea L, et al. GM-CSF: a role in immune and inflammatory reactions in the intestine, Expert Rev Gastroenterol Hepatol 4:723-31 (2010).
Egea L, et al., GM-CSF Prooduced by Nonhematopoietic Cells is Required for Early Epithelial Cell Proliferation and Repair of Injured Colonic Mucosa, J Immunol 190:1702-13 (2013).
Felici et al., Phage-Displayed Peptides as Tools for Characterization of Human Sera, in Abelson (Ed.), Methods in Enzymol. 267, San Diego: Academic Press, Inc. (1996).
Foell D, et al., Neutrophil derived fuman S100A12 (EN-RAGE) is strongly expressed during chronic active inflammatory bowel disease, Gut 52:847-53(2003).
Fudala R, et al., Anti-interleukin-8 autoantibody: interleukin-8 immune complexes in acute lung injury/acute respiratory distress syndrome, Clin Sci (Lond)114:403-12 (2008).
Gathungu G, et al. Granulocyte-macrophage colony-stimulating factor auto-antibodies: a marker of aggressive crohn's disease, Inflamm Bowel Dis 19(8):1671-1680 (2013).
Han X, et al., Granulocyte-Macrophage Colony-Stimulating Factor Autoantibodies in Murine ileitis and Progressive Ileal Crohn's Disease, Gastroenterology 136:1261-71, e1-3 (2009).
Harlow and Lane, Antibodies a Laboratory Manual Cold Spring Harbor Laboratory: New York, 1988.
Hyams JS, et al., Development and validation of a Pediatric Crohn's Disease Activity Index, J Pediatr Gastroenterol Nutr 12:439-47 (1991).
Judd TA, et al., Update of fecal markers of inflammation in inflammatory bowel disease, J Gastroenterol Hepatol 26:1493-9 (2011).
Jurickova I, et al., Paediatric Crohn disease patients with structuring behavior exhibit ileal granulocyte-macrophage colony-stimulating factor (GM-CSF) autoantibody production and reduced neutrophil bacterial killing and GM-CSF bioactivity, Clin Exp Immunol 172:455-465 (2013).
Kelsen JR, et al., Phase I Trial of Sargramostim in Pediatric Crohn;s Disease, Inflamm Bowel Dis 16:1203-8 (2010).
Korzenik JR, et al. Sargramostim for active Chron's Disease, N Engl J Med 352:2193-201 (2005).
Langhorst J, Fecal Lactoferrin as a Noninvasive Biomarker in Inflammatory Bowl Diseases, Boone J. Drugs Today (Barc) 48:149-61 (2012).
Langhorst J, et al. Noninvasive Markers in the Assessment of Intestinal Inflammation in Inflammatory Bowel Diseases: Performance of Fecal Lactoferrin, Calprotectin, and PMN-Elastase, CRP and Clinical Indices, Am J Gastroenterol 103:162-9 (2008).
Mao R, et al. Fecal calprotectin in predicting relapse of inflammatory bowel diseases: a meta-analysis of prospective studies. Inflamm Bowel Dis 18:1894-9 (2012).
McHugh et al., Development of a microsphere-based fluorescent immunoassay and its comparison to an enzyme immunoassay for the detection of antibodies to three antigen preparations from *Candida albicans*, J. Immunol. Methods 116:213-219 (1989).
Nylund CM, et al., Granulocyte Macrophage-Colony-stimulating Factor Autoantibodies and Increased Intestinal Permeability in Crohn Disease, J Pediatr Gastroenterol Nutr 52:542-8 (2011).
Price J.V. et al., Protein microarray analysis reveals BAFF-binding autoantibodies in systemic lupus erythematosus, J Clin. Invest. 123:5135-5145 (2013).
Rachmilewitz D., Coated mesalazine (5-aminosalicylic acid) versus sulphasalazine in the treatment of active ulcerative colitis: a randomized trial, BMJ 298:82-6 (1989).
Rosen L.B. et al., Anti-GM-CSF Autoantibodies in Patients with Crypotcoccal Meningitis, J Immunol 190:3959-3966 (2013).
Rosenau BJ, Schur PH., Autoantibodies to Tumor Necrosis Factor in Patients with Rheumatoid Arthritis and Systemic Lupus Erythematosus, J Rheumatol 36:753-756 (2009).
Sainathan SK, et al., Granulocyte marcophange colony stimulating factor ameliorates DSS induced experimental colitis, Inflamm Bowel Dis 14:88-99 (2008).
Samson CM, et al., Improved Outcomes with Quality Improvement Interventions in Pediatric Inflammatory Bowel Disease, J Pediatr Gastroenterol Nutr 55:679-88 (2012).
Sandborn WJ, et al., A Review of Activity Indices and Efficacy Endpoints for Clinical Trials of Medical Therapy in Adults with Crohn's Disease, Gastroenterology 122:512-30 (2002).
Sartor RB., Mechanisms of Disease: pathogenesis of Crohn's disease and ulcerative colitis, Nat Clin Pract Gastroenterol Hepatol 3:390-407 (2006).
Schmalzing and Nashabeh, Capillarty electrophoresis based immunoassays: A critical review. Electrophoresis 18:2184-93 (1997).
Scillian et al., Early Detection of Antibodies Against rDNA-Produced HIV Proteins with a Flow Cytomertric Assay, Blood 73:2041 (1989).
Self and Cook, Advances in immunoassay technology, Curr. Opin. Biotechnol. 7:60-65 (1996).
Siegel CA, et al. Real-time Tool to Display the Predicted Disease Course and Treatment Response for Children with Chron's Disease, Inflamm Bowel Dis 17:30-8 (2011).
Turner D, et al., Development, Validation, and Evaluation of a Pediatric Ulcerative Colitis Activity Index: A Prospective Multicenter Study, Gastroenterology 133:423-32 (2007).
Uchida K, et al. Granulocyte/macrophage-colony-stimulating factor autoantibodies and myeloid cell immune functions in healthy subjects, Blood 113:2547-56 (2009).
Valentine JF, et al. Steroid-sparing properties of sargramostim in patients with corticosteroid-dependent Crohn's disease: a randomized, double-blink, placebo-controlled, phase 2 study, Gut 58:1354-62 (2009).
Watanabe M, et al. High avidity cytokine autoantibodies in health and disease: Patogenesis and mechanisms, Cytokine Growth Factor Rev 21:263-73 (2010).

\* cited by examiner

METHODS AND COMPOSITIONS FOR DETERMINING AND TREATING RELAPSE IN INFLAMMATORY BOWEL DISEASE

RELATED APPLICATIONS

This application is the U.S. national phase of International Application No. PCT/US2014/037927 filed May 13, 2014 and published in English as WO 2014/186416 on Nov. 20, 2014 which claims the benefit of U.S. Provisional Application No. 61/823,323 entitled METHODS AND COMPOSITIONS FOR DETERMINING RELAPSE IN INFLAMMATORY BOWEL DISEASE filed May 14, 2013, which is incorporated herein by reference in its entirety.

STATEMENT REGARDING FEDERALLY SPONSORED R&D

This invention was made with government support under DK078683 awarded by the National Institutes of Health. The government has certain rights in the invention.

FIELD OF THE INVENTION

The present invention relates to evaluating relapse risk in subjects having an inflammatory bowel disease (IBD). Some embodiments include selecting a treatment for an evaluated IBD relapse risk in a subject.

BACKGROUND OF THE INVENTION

The clinical course of inflammatory bowel diseases (IBDs) is variable. The best outcomes include only a 65% rate of sustained remission—in other words, at least 35% of patients receiving standardized care will experience at least one relapse over the course of a year (Crandall W V, et al. Pediatrics 2012; 129:e1030-41; Samson C M, et al. J Pediatr Gastroenterol Nutr 2012; 55:679-88). Approximately 15% of patients ultimately do not respond to medical therapy and require surgery for stricturing/penetrating behavior within three years of diagnosis (Siegel C A, et al. Inflamm Bowel Dis 2011; 17:30-8). These varied outcomes are likely due to substantial genetic, microbial, and immune heterogeneity in disease pathogenesis (Sartor R B. Nat Clin Pract Gastroenterol Hepatol 2006; 3:390-407). Clinical tools and biomarkers to define important patient subsets are lacking. While earlier use of anti-tumor necrosis factor (TNF) therapy is likely to improve rates of sustained remission and reduce rates of surgery, there are currently no diagnostic tools with sufficient accuracy to predict either relapse, structuring, or continued remission, and thereby guide selection of appropriate therapies, such as introduction of anti-TNF when it is likely to provide the greatest benefit (Colombel J F, et al. N Engl J Med 2010; 362:1383-95).

SUMMARY OF THE INVENTION

Some embodiments of the methods and compositions provided herein relate to a method of selecting a treatment for a subject having inflammatory bowel disease (IBD). Some such methods include measuring the level of an anti-GM-CSF antibody in a sample from said subject, thereby determining the IBD relapse risk for said subject; and selecting a treatment for said IBD relapse risk.

In some embodiments, methods of selecting a treatment for a subject having inflammatory bowel disease (IBD) include measuring the level of an anti-GM-CSF antibody in a sample from said subject, thereby evaluating the IBD relapse risk for said subject; and providing the IBD relapse risk to a party in order for said party to select a treatment for said subject.

Some embodiments of the methods and compositions provided herein relate to a method of predicting relapse risk in a subject having inflammatory bowel disease (IBD). Some such methods include measuring the level of an anti-GM-CSF antibody in a sample from said subject; and providing the result of said measuring to a party in order for said party to evaluate IBD relapse risk for said subject. Some embodiments also include selecting a treatment for said subject for said IBD relapse risk.

In some embodiments, the party is a physician.

Some embodiments also include comparing the level of the anti-GM-CSF antibody in a sample from said subject with the level of the anti-GM-CSF antibody in a sample obtained from said subject at a prior time or a sample obtained from a subject without said IBD.

In some embodiments, an increase in the level of the anti-GM-CSF antibody in a sample from said subject compared to the level of the anti-GM-CSF antibody in a sample obtained from said subject at a prior time indicates an increased IBD relapse risk.

In some embodiments, a decrease in the level of the anti-GM-CSF antibody in a sample from said subject compared to the level of the anti-GM-CSF antibody in a sample obtained from said subject at a prior time indicates a decreased IBD relapse risk.

In some embodiments, no substantial change in the level of the anti-GM-CSF antibody in a sample from said subject compared to the level of the anti-GM-CSF antibody in a sample obtained from said subject at a prior time indicates a decreased IBD relapse risk.

In some embodiments, the IBD relapse risk comprises an increased IBD relapse risk within about 9 months. In some embodiments, the IBD relapse risk comprises an increased IBD relapse risk within about 6 months. In some embodiments, the IBD relapse risk comprises an increased IBD relapse risk within about 3 months. In some embodiments, the IBD relapse risk comprises an increased IBD relapse risk within about 2 month. In some embodiments, the IBD relapse risk comprises an increased IBD relapse risk within about 1 month.

In some embodiments, the level of the anti-GM-CSF antibody in said sample indicates an increased relapse risk.

In some embodiments, the level of the anti-GM-CSF antibody in said sample indicates a decreased relapse risk.

In some embodiments, the measuring comprises contacting the sample with an antibody or antigen-binding fragment thereof.

In some embodiments, the measuring is performed in an automated device.

In some embodiments, the treatment comprises maintaining remission.

In some embodiments, the treatment comprises inducing remission.

In some embodiments, the treatment is selected from the group consisting of a corticosteroid, a 5-aminosalicylate, azathioprine, 6-mercaptopurine, a TNF inhibitor, methotrexate, and surgery.

In some embodiments, the IBD is selected from the group consisting CD and UC. In some embodiments, the CD is selected from the group consisting of illeal CD, colonic CD, illeo-colic CD, and upper gastrointestinal CD. In some embodiments, the UC is selected from the group consisting of ulcerative proctitis, left-sided colitis, and pancolitis.

Some embodiments also include obtaining a sample from said subject.

In some embodiments, the sample comprises serum.

In some embodiments, the sample is ex vivo.

Some embodiments also include measuring the level of fecal S100A8/A9 in a fecal sample from said subject.

In some embodiments, the subject is human.

BRIEF DESCRIPTION OF THE DRAWINGS

FIG. 1A illustrates GM-CSF Ab concentrations in correlation with disease activity (active disease versus remission). FIG. 1B illustrates levels of GM-CSF Ab at different time points before, during and after disease relapse (Vst±3: study visit 7 to 9 months before/after relapse; Vst±2: study visit 4 to 6 months before/after relapse; Vst±1: study visit 2 to 3 month before/after relapse). FIG. 1C illustrates GM-CSF Ab concentrations in correlation with disease location in CD and extent of UC as assessed by the Montreal classification (ileal CD [L1], colonic CD [L2], ileo-colonic CD [L3], concomitant upper gastrointestinal disease [L4]; ulcerative proctitis [E1], left-sided or distal colitis [E2], and extensive colitis [E3]). FIG. 1D illustrates GM-CSF Ab concentrations at various times.

FIG. 2A and FIG. 2B are ROC curve analyses relating to the sensitivity and specificity of GM-CSF Ab in differentiating patients with CD and UC, respectively, with disease relapse from patients in remission during the visits 2 to 6 month before the relapse becomes clinically apparent. FIG. 2C and FIG. 2D are Kaplan-Meier time-to-relapse curves for patients with CD and UC, respectively, and illustrate the difference in the proportion of patients who relapsed over a 1.5-year period depending on the GM-CSF Ab concentration at the time of inclusion into the study.

DETAILED DESCRIPTION

Figure 1A:
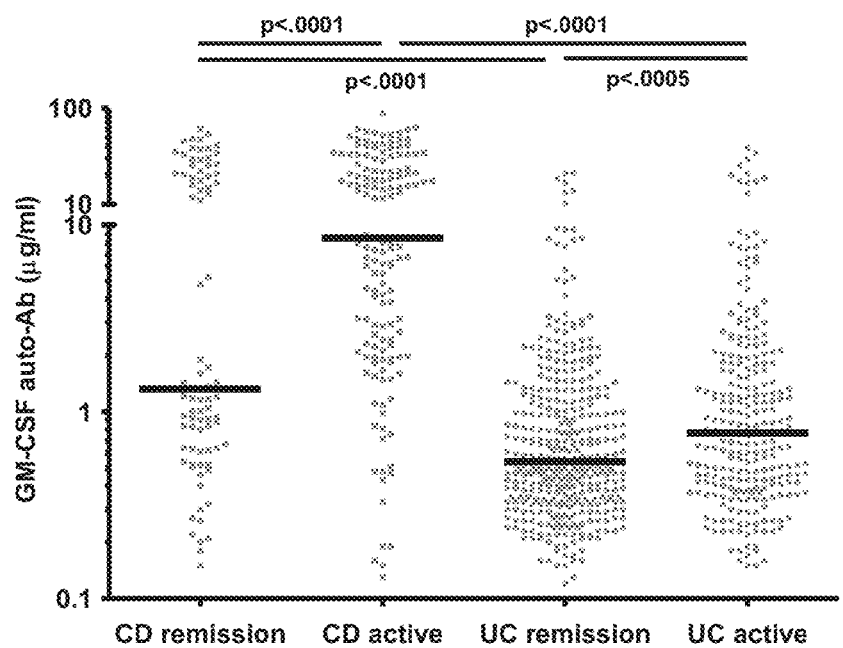
FIGS. 1A-1D are scatter plots that show the median levels (central horizontal line) of GM-CSF Ab levels in serum samples of pediatric and adult patients with CD and UC, with P values shown, and illustrate the correlation of serum GM-CSF Ab with activity, location and extent of IBD.

The present invention relates to methods and compositions for evaluating relapse risk in subjects having an inflammatory bowel disease (IBD). Some embodiments include selecting a treatment for an evaluated IBD relapse risk in a subject. In particular, Applicants have discovered that an increase in anti-GM-CSF antibodies in subjects with IBD can be useful to predict IBD relapse in a subject. Determination of relapse risk is useful to select and provide an appropriate treatment to the subject. In addition, Applicants have discovered that other biomarkers such as fecal S100A8/A9 are also associated with IBD relapse risk.

A recent bioinformatics analysis identified a role for granulocyte-macrophage colony stimulating factor (GM-CSF) signaling in the pathogenesis of Crohn's disease (CD). Egea L, et al. J Immunol 2013; 190:1702-13. GM-CSF is a cytokine that promotes myeloid cell development and maturation, and dendritic cell differentiation and survival in vitro. Growing evidence supports the notion that GM-CSF exerts pleotropic effects in the gut and has an important role in the regulation of mucosal injury, intestinal immune and inflammatory responses. Egea L, et al. Expert Rev Gastroenterol Hepatol 2010; 4:723-31. GM-CSF reduces chemically induced gut injury in mice, and clinical trials of GM-CSF in CD have demonstrated a reduction in disease activity in some patients. Bernasconi E, et al. Inflamm Bowel Dis 2010; 16:428-41; Dranoff G. Gastroenterology 2011; 141:28-31; Kelsen J R, et al. Inflamm Bowel Dis 2010; 16:1203-8; Korzenik J R, et al. N Engl J Med 2005; 352:2193-201; Sainathan S K, et al. Inflamm Bowel Dis 2008; 14:88-99; and Valentine J F, et al. Gut 2009; 58:1354-62.

Furthermore, endogenous cytokine auto-antibodies (Ab) have been described in healthy individuals and those with chronic inflammatory disorders. Watanabe M, et al. Cytokine Growth Factor Rev 2010; 21:263-73. Cytokine Ab may exert neutralizing, activating, or no effect upon the target cytokine. Fudala R, et al. Clin Sci (Lond) 2008; 114:403-12; Rosenau B J, Schur P H. J Rheumatol 2009; 36:753-6; and Browne S K, et al. Curr Opin Allergy Clin Immunol 2010; 10:534-41. While the therapeutic use of anti-cytokine monoclonal antibodies in IBD has been the focus of intense investigation over the past decade, the role of endogenous cytokine Ab in regulating mucosal immunity and patient outcomes has received relatively little attention. In one study, IBD patients with higher TNFα neutralizing capacity due to endogenous TNFα Ab exhibited a lower rate of clinical response to infliximab administration. Ebert E C, et al. Clin Exp Immunol 2008; 154:325-31.

Prior studies have examined the role of endogenous GM-CSF Ab as a regulator of myeloid cell function, and biomarker for disease activity and stricturing in CD. GM-CSF Ab production was found to be enriched within the strictured ileum in CD, and high titers of GM-CSF Ab were associated with reduced GM-CSF bioactivity and neutrophil bacterial killing as well as increased intestinal permeability and anti-microbial seroreactivity. Han X, et al. Gastroenterology 2009; 136:1261-71, e1-3; Nylund C M, et al. J Pediatr Gastroenterol Nutr 2011; 52:542-8; Jurickova I, et al. Clin Exp Immunol 2013; Gathungu G, et al. Inflamm Bowel Dis 2013; and Uchida K, et al. Blood 2009; 113:2547-56.

Moreover, the factors which promote clinical relapse in IBD are poorly understood. Endogenous cytokine auto-antibodies play a role in a number of auto-immune and chronic inflammatory disorders (Watanabe M, et al. Cytokine Growth Factor Rev 2010; 21:263-73). Given the advent of therapeutic anti-cytokine antibody use in IBD, a better understanding of the role of endogenous cytokine auto-antibodies in pathogenesis and treatment response is potentially of great importance (Danese S. Gut 2012; 61:918-32). Elevated levels of GM-CSF Ab are associated with an increase in intestinal permeability, increased titers of several anti-microbial seroreactivities, and increased rates of stricturing behavior and surgery in adult and pediatric CD (Han X, et al. Gastroenterology 2009; 136:1261-71, e1-3; and Nylund C M, et al. J Pediatr Gastroenterol Nutr 2011; 52:542-8). Accurate monitoring of intestinal inflammation relies on clinical indices (based on symptoms and clinical examination) and endoscopy, in conjunction with histologic investigation and imaging techniques. In recent decades, a number of fecal biomarkers have been evaluated for their ability to differentiate and monitor IBD disease activity but an ideal fecal marker for IBD has yet to be identified (Dabritz J, et al. Inflamm Bowel Dis 2013 Jan. 31; Epub; Foell D, et al. Gut 2009; 58:859-68; Judd T A, et al. J Gastroenterol Hepatol 2011; 26:1493-9; Mao R, et al. Fecal calprotectin in predicting relapse of inflammatory bowel diseases: a meta-analysis of prospective studies. Inflamm Bowel Dis 2012; 18:1894-9; and Langhorst J, Boone J. Drugs Today (Barc) 2012; 48:149-61; Langhorst J, et al. Am J Gastroenterol 2008; 103:162-9).

Embodiments relate to the discovery that GM-CSF Ab titers can be a suitable marker for confirming the stable remission, or predicting a relapse, of IBD during long-term follow-up. To investigate the accuracy of serum GM-CSF Ab levels in predicting relapse of IBD, GM-CSF Ab levels in prospectively collected serum samples of patients with CD and UC were examined. Time course analysis of GM-CSF Ab up to 9 months before and after relapse showed a clear increase of Ab titers up to 6 months before clinical relapse followed by a steady decrease, likely indicating the success of the intensified therapies. Thus, an elevated serum GM-CSF Ab titer in patients with IBD in clinical remission as defined by clinical disease activity indices may represent an early stage of increased intestinal permeability, bacterial translocation, neutrophil dysfunction, and reduced antimicrobial activity.

The results described herein indicate that measuring GM-CSF Ab levels may serve as a tool for monitoring relapses and for measuring the effects of treatment. In one experiment, a baseline GM-CSF level of >1.7 µg/mL was significantly associated with relapse of CD within 18 months. At 1.72 µg/mL the sensitivity and specificity of GM-CSF Ab for predicting relapse of CD already 2 to 6 months earlier were 88% and 95%, respectively. Previously, Han et al. have previously defined elevated GM-CSF Ab as a serum concentration ≥1.7 µg/mL. In contrast to fecal S100 proteins, embodiments described herein show that GM-CSF Ab levels are a stronger predictor of relapse in CD than in UC. Thus, the combined determination of biomarkers, e.g. the measurement of GM-CSF Ab levels and fecal S100 protein concentrations, could be useful to assess the risk of relapses in patients with IBD, both with CD and UC.

Definitions

As used herein "subject" includes a vertebrate, such as a mammal, such as a human, such as a human patient having IBD.

As used herein a "sample" includes any sample obtained from a living system or subject, including blood, serum, tissue. In some embodiments, a sample is obtained through sampling by minimally invasive or non-invasive approaches (e.g., urine collection, stool collection, blood drawing, needle aspiration, and other procedures involving minimal risk, discomfort or effort). Samples can be gaseous (e.g., exhaled breath), or liquid/fluid. Liquid samples include, but are not limited to, urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, and others. Samples also include a clinical sample such as serum, plasma, other biological fluid, or tissue samples, and also includes cells in culture, cell supernatants and cell lysates. Samples can be in vivo or ex vivo.

Inflammatory Bowel Diseases

Examples of IBDs include Crohn's disease (CD) and Ulcerative colitis (UC). Crohn's disease can include illeal CD, colonic CD, illeo-colic CD, and upper gastrointestinal CD. Ulcerative colitis can include ulcerative proctitis, left-sided colitis, and pancolitis.

Methods to Evaluate Relapse Risk and Treat IBD Subjects

Some embodiments of the methods and compositions provided herein relate to evaluating a subject having IBD for IBD relapse risk. Some embodiments include measuring the level of an anti-GM-CSF antibody in a sample from said subject. Methods to measure the level of an anti-GM-CSF antibody in a sample are well known in the art, examples of which are provided herein. Measuring the level of an anti-GM-CSF antibody in a sample can be performed by automated devices. In some embodiments, measuring the level of an anti-GM-CSF antibody in a sample can determine the relative risk of a subject having an IBD having a relapse. For example, an increased level of an anti-GM-CSF antibody in a sample can be indicative of an increased risk of relapse. Conversely, a decreased level of an anti-GM-CSF antibody in a sample can be indicative of a decreased risk of relapse. In some embodiments, no substantial change in the relative level of the anti-GM-CSF antibody in a sample can indicate a decreased IBD relapse risk. In some embodiments, an additional biomarker can be measured in a sample from the subject that is indicative of the relative risk of IBD relapse. In some embodiments, an additional biomarker can include fecal S100A8/A9. In some such embodiments, a fecal sample can be obtained from the subject. Methods to measure the level of fecal S100A8/A9 in a sample are well known in the art.

In some embodiments, the level of an anti-GM-CSF antibody in a sample from a subject having IBD can be compared to the level of an anti-GM-CSF antibody in a sample obtained from the subject at a prior time, or in a sample obtained from another subject without IBD. In some embodiments, a sample obtained from the subject at a prior time can include a sample obtained at least about 1 day, 2 days, 5 days, 10 days, 30 days, 50 days, 100 days, 200 days, 500 days, or more, previous to the instant sample.

In some embodiments, the level of an anti-GM-CSF antibody in a sample, the relative change in the level of an anti-GM-CSF antibody in a sample, and/or an evaluated IBD relapse risk of a subject can be provided to a party. A party can include a physician. In some embodiments, the party can evaluate IBD relapse risk in a subject, selected a treatment for the subject with the evaluated IBD relapse risk, and/or administer the treatment. In some embodiments, the level of an anti-GM-CSF antibody in a sample, the relative change in the level of an anti-GM-CSF antibody in a sample, and/or an evaluated IBD relapse risk of a subject can be provided to an automated system. In some such embodiments, an IBD relapse risk for a subject having an IBD can be evaluated, and/or a treatment selected for the subject with the evaluated IBD relapse risk.

In some embodiments, the level of an anti-GM-CSF antibody in a sample can indicate that a subject having an IBD is likely to have a relapse within a certain period, and therefore, the subject has an increased IBD relapse risk within that period. In some embodiments, the IBD relapse risk comprises an increased IBD relapse risk within about 12 months, 10 months, 9 months, 6 months, 5 months, 4 months, 3 months, 2 months, and 1 month.

Methods of Treatment

Embodiments of the methods and compositions provided herein include treating subjects having an IBD with an evaluated risk of IBD relapse. Examples of treatments include: corticosteroids, used primarily for treatment of moderate to severe flares of IBDs, such as CD, examples include prednisone and budesonide; 5-aminosalicylates, useful in the treatment of mild-to-moderate IBDs, such as CD, examples include 5-aminosalicylic acid (mesalazine), and sulfasalazine; Azathioprine and 6-mercaptopurine (6-MP) for maintenance therapy of IBDs, such as CD; TNF inhibitors useful for treating various severities of IBDs, such as CD, examples include infliximab, adalimumab, natalizumab; methotrexate; and surgery.

In some embodiments, selecting treatment for such subjects can include selecting treatment to maintain remission. In some embodiments, selecting treatment for such subjects can include selecting treatment to induce remission. In some embodiments, selecting treatment for such subjects can include selecting treatment to treat acute symptoms.

In an example embodiment, a subject having a GM-CSF antibody level that meets or exceeds a threshold level that is indicative of an increased risk of relapse, a party, such as a physician may verify and select certain treatments. For example, the party can verify adherence to prescribed medications/treatments; the party can verify optimal dosing for the medications/treatments; and/or the party can adjust the dosing of current medications/treatments. In some embodiments, the party can select a medication/treatment to prevent relapse. For example, if a subject is being treated with a thiopurine, 6-mercaptopurine or azathioprine, and the subject's level of GM-CSF antibody increases, the subject's level of 6TG can be tested. If the subject's level of 6TG is optimal, the party may consider an alternative treatment, such as anti-TNF to prevent relapse. In some embodiments, treatment can be selected that includes improving a subject's adherence to a current medication/treatment. In some embodiments, treatment can be selected that includes modifying the dose of a current medication/treatment.

Methods to Detect and Measure the Level of Anti-GM-CSF Antibody

Methods to detect and measure the level of anti-GM-CSF antibody in a sample are well known in the art. Examples are provided in U.S. Patent Application No. 2010/0255513, which is incorporated herein by reference in its entirety. The following provides example methods Flow cytometry can be used to determine anti-GM-CSF antibody levels in a sample. Such flow cytometric assays, including bead based immunoassays, can be used to determine anti-GM-CSF antibody levels in the same manner as used to detect serum antibodies to Candida albicans and serum antibodies to HIV proteins (See e.g., Bishop and Davis, J. Immunol. Methods 210:79-87 (1997); McHugh et al., J. Immunol. Methods 116:213 (1989); Scillian et al., Blood 73:2041 (1989), each of which is incorporated by reference herein).

Phage display technology for expressing a recombinant antigen specific for anti-GM-CSF antibodies also can be used to determine the level of anti-GM-CSF antibody. Phage particles expressing the antigen specific for anti-GM-CSF antibody, or an antigen specific for anti-GM-CSF antibody, can be anchored, if desired, to a multiwell plate using an antibody such as an antiphage monoclonal antibody (Felici et al., "Phage-Displayed Peptides as Tools for Characterization of Human Sera" in Abelson (Ed.), Methods in Enzymol. 267, San Diego: Academic Press, Inc. (1996), which is incorporated by reference herein).

A variety of immunoassay formats including competitive and non-competitive immunoassay formats also are useful (Self and Cook, Curr. Opin. Biotechnol. 7:60-65 (1996), which is incorporated by reference). Immunoassays encompass capillary electrophoresis based immunoassays (CEIA) and can be automated, if desired. Immunoassays also can be used in conjunction with laser induced fluorescence (See e.g., Schmalzing and Nashabeh, Electrophoresis 18:2184-93 (1997)); Bao, J. Chromatogr. B. Biomed. Sci. 699:463-80 (1997), each of which is incorporated herein by reference). Liposome immunoassays, such as flow-injection liposome immunoassays and liposome immunosensors, also can be used to determine anti-GM-CSF antibody concentration.

Immunoassays, such as enzyme-linked immunosorbent assays (ELISAs), can be particularly useful. An ELISA, for example, can be useful for determining whether a sample is positive for anti-GM-CSF antibodies or for determining the anti-GM-CSF antibody level in a sample. An enzyme such as horseradish peroxidase (HRP), alkaline phosphatase (AP), β-galactosidase or urease can be linked to a secondary antibody selective for anti-GM-CSF antibody, or to a secondary antibody selective for anti-GM-CSF antibody for use in the methods and compositions provided herein. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm, or a urease detection system can be used with a substrate such as urea-bromocresol purple (Sigma Immunochemicals, St. Louis, Mo.). A useful secondary antibody linked to an enzyme can be obtained from a number of commercial sources; goat F(ab').sub.2 anti-human IgG-alkaline phosphatase, for example, can be purchased from Jackson Immuno-Research (West Grove, Pa.).

A radioimmunoassay also can be useful for determining the level of anti-GM-CSF antibodies in a sample. A radioimmunoassay using, for example, an iodine$^{125}$ labeled secondary antibody (Harlow and Lane, Antibodies A Laboratory Manual Cold Spring Harbor Laboratory: New York, 1988, which is incorporated herein by reference) is encompassed within the methods and compositions provided herein.

A secondary antibody labeled with a chemiluminescent marker also can be useful in the methods and compositions provided herein. Such a chemiluminescent secondary antibody is convenient for sensitive, non-radioactive detection of anti-GM-CSF antibodies and can be obtained commercially from various sources such as Amersham Lifesciences, Inc. (Arlington Heights, Ill.).

In addition, a detectable reagent labeled with a fluorochrome can be useful in the methods and compositions provided herein for determining the levels of anti-GM-CSF antibody in a sample. Appropriate fluorochromes include, for example, DAPI, fluorescein, Hoechst. 33258, R-phycocyanin, B-phycoerythrin, R-phycoerythrin, rhodamine, Texas red or lissamine. A particularly useful fluorochrome is fluorescein or rhodamine. Secondary antibodies linked to fluorochromes can be obtained commercially. For example, goat F(ab')$_2$ anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of iodine$^{125}$; or a fluorometer to detect fluorescence in the presence of light of a certain wavelength. For detection of enzyme-linked reagents, a quantitative analysis of the amount of anti-GM-CSF antibody can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Immunoassays using a secondary antibody selective for anti-GM-CSF antibodies are particularly useful in the methods and compositions provided herein. As used herein, the term "antibody" means a population of immunoglobulin molecules, which can be polyclonal or monoclonal and of any isotype. As used herein, the term "antibody" encompasses an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

Some embodiments of the methods and compositions provided herein can include measuring the level of anti-GM-CSF antibodies in a sample using a microarray (See e.g., Price J. V. et al., (2013) J Clin. Invest. 123:5135-5145, which is incorporated herein by reference in its entirety). In some embodiments, a microarray can include a nitrocellulose surface microarray platform containing GM-CSF. The GM-CSF can be printed on to a nitrocellulose-surface glass slides using a robotic microarrayer (VersArray ChipWriter Compact) and software (ChipWriter Pro, BioRad) in replicates and across a range of concentrations. The array can be blocked in a protein solution, rinsed, and sample added comprising a primary anti-GMCSF antibody, such as anti-GMCSF mAb control (catalog no. 554502, Beckton Dickinson). The array is incubated, rinsed, and a fluorescently conjugated secondary antibody specific for the Fc region of the primary antibody probe. To visualize reactive features, we scanned processed arrays using an Axon™ digital microarray scanning system, and quantified median fluorescence intensity as a measure of primary antibody reactivity.

Some embodiments of the methods and compositions provided herein can include measuring the level of anti-GM-CSF antibodies in a sample using particle-based technologies (See e.g., Rosen L. B. et al., (2013) Journal of Immunology 190:3959-3966; and Ding L. et al., (2012) J. Clin. Immunol. 32: 238-245, which are incorporated herein by reference in their entireties). In some embodiments, fluorescing magnetic beads are conjugated to GM-CSF and beads are combined and incubated for 1 h with subject or control plasma at 1:100 dilution, washed, and incubated with biotinylated mouse anti-human total IgG, as well as IgG subclasses, and IgA, IgM, and IgE (Sigma). Beads are washed again and incubated with Streptavidin-PE (Bio-Rad) before being run in a multiplex assay on the Bio-Plex (Bio-Rad) instrument. Fluorescence intensity for each bead type is plotted as a function of Ab titer (GraphPad Prism, version 5.0c).

EXAMPLES

Example 1—Correlation Between GM-CSF Auto-Antibodies and Disease Relapse in IBD

In a prospective multicenter study pediatric and adult patients with CD and UC in remission were consecutively recruited and followed up for a period of 38 months. Study design and clinical classifications have been reported in Dabritz J, et al. "Improving Relapse Prediction in Inflammatory Bowel Disease by Neutrophil-Derived S100A12" Inflamm Bowel Dis 2013 Jan. 31, Epub, incorporated herein by reference in its entirety. Ethical approval was obtained and fully written informed consent was obtained from all patients or legal guardians.

Assessment of Disease Activity

Disease activity in CD patients was determined by a disease activity assessment based on the CD activity index (CDAI) and pediatric CD activity index (PCDAI). Sandborn W J, et al. Gastroenterology 2002; 122:512-30; and Hyams J S, et al. J Pediatr Gastroenterol Nutr 1991; 12:439-47, which are incorporated herein by reference in their entireties. Disease activity in UC patients was determined by a disease activity assessment based on the UC activity index (UCAI) and pediatric UC activity index (PUCAI). Rachmilewitz D. BMJ 1989; 298:82-6; and Turner D, et al. Gastroenterology 2007; 133:423-32, which are incorporated herein by reference in their entireties. Example definitions of disease remission and relapse are summarized in Table 1.

TABLE 1

| Activity index | Remission | Relapse |
|---|---|---|
| CDAI | <150 AND <Δ70 points/2 weeks | ≥Δ70 points/2 weeks |
| PCDAI | <11 AND <Δ5 points/2 weeks | ≥Δ5 points/2 weeks |
| UCAI | <5 AND <Δ3 points/2 weeks | ≥Δ3 points/2 weeks |
| PUCAI | <10 AND <Δ5 points/2 weeks | ≥Δ5 points/2 weeks |

Stool and Serum Analysis

Stool and serum samples were coded and stored at −80° C. before analysis. Serum concentrations of GM-CSF autoantibodies were quantified by ELISA. See e.g., Han X, et al. Gastroenterology 2009; 136:1261-71, e1-3, which is incorporated herein by reference in its entirety. Concentrations of fecal S100A12 were determined by a double-sandwich ELISA, as described previously in Foell D, et al. Gut 2003; 52:847-53, which is incorporated herein by reference in its entirety. Fecal calprotectin (S100A8/A9) concentrations were also determined by ELISA (Immundiagnostik AG, Bensheim, Germany). The readers of the assays were blinded for diagnosis and disease stage.

Statistical Analysis

For continuous variables, median and range were documented except when otherwise stated. For categorical variables, percentages are provided. Statistical comparisons of data between groups were tested by 2-sided Mann-Whitney U test. The correlations between serum GM-CSF Ab levels and clinical disease activity indices, full blood count parameters, CRP, and ESR were calculated using Spearman's rho correlation coefficient. Time-to-relapse analyses were performed using Kaplan-Meier curves, and differences between the groups were evaluated with the log-rank test. To determine the accuracy of serum GM-CSF Ab measurements as a prognostic test receiver operating characteristics (ROC) curves were drawn by plotting sensitivity against 1-specificity. Overall accuracy of the marker in detecting IBD relapse was represented by area under the curve (AUC) with 95% confidence interval. Best cutoff point was defined as the maximum sum of sensitivity and specificity. A P value<0.05 was considered statistically significant. All calculations were performed by using GraphPad Prism Version 5.00 for Windows (GraphPad Software, La Jolla, Calif., USA).

Clinical and Demographic Characteristics

In total, 181 patients with IBD (61 with CD and 120 with UC) were prospectively included in the study. Clinical and demographic characteristics of the study subjects are summarized in Table 2.

TABLE 2

| | Characteristic | Crohn's disease | Ulcerative colitis |
|---|---|---|---|
| | Patients, n (%) | 61 (34) | 120 (66) |
| Age | All, years (range) | 23.4 (3.5-53.9) | 44.7 (9.2-74.6) |
| | <16, n (%) | 24 (39) | 10 (8) |
| | 17-40, n (%) | 28 (46) | 34 (28) |
| | >40, n (%) | 9 (15) | 76 (63) |
| | At diagnosis, years (range) | 14.6 (3.4-35.2) | 31.2 (6.5-72.1) |

TABLE 2-continued

| Characteristic | | Crohn's disease | Ulcerative colitis |
|---|---|---|---|
| Sex | Male, n (%) | 27 (44) | 55 (46) |
| | Female, n (%) | 34 (56) | 65 (54) |
| | Ratio, male/female | 0.79 | 0.85 |
| Localization (%) | Ileal | 11 | — |
| | Colonic | 20 | — |
| | Ileo-colonic | 70 | — |
| | Upper gastrointestinal disease | 13 | — |
| | Ulcerative proctitis | — | 18 |
| | Left-sided colitis | — | 49 |
| | Pancolitis | — | 33 |
| Patients with relapse | All, n (%) | 37 (61) | 53 (44) |
| | Time, weeks (range) | 38 (3-99) | 20 (4-118) |
| | Severe disease, n (%) | 8 (22) | 33 (62) |
| Observation period | Duration, weeks (range) | 31 (0-147) | 46 (0-120) |
| | Visits, n | 286 | 657 |
| | Serum samples, n | 233 | 628 |
| | Stool samples, n | 132 | 478 |
| Medication, n (%) | No medication | 9 (18) | 47 (39) |
| | Oral corticosteroids | 23 (38) | 12 (10) |
| | 5-aminosalicylates | 17 (28) | 64 (53) |
| | Azathioprine | 22 (36) | 8 (7) |
| | Anti-TNFα agents | 19 (31) | 3 (3) |
| | Methotrexate | 3 (5) | 1 (1) |

Serum GM-CSF Ab and Monitoring of Disease Activity

GM-CSF Ab were significantly higher in patients with active CD (8.5 µg/mL; 0.1-576 µg/mL; n=150) compared with patients with CD in remission (1.3 µg/mL; 0.2-61 µg/mL; n=83; P<0.0001). See FIG. 1A. Likewise, GM-CSF Ab were higher in active UC (0.8 µg/mL; 0.1-38 µg/mL; n=253) than in inactive UC (0.5 µg/mL; 0.02-21 µg/mL; n=374; P<0.0005). Furthermore, GM-CSF Ab levels were higher in CD (both during active disease and remission) compared with GM-CSF Ab levels in serum samples of patients with UC (P<0.0001).

Figure 1B:
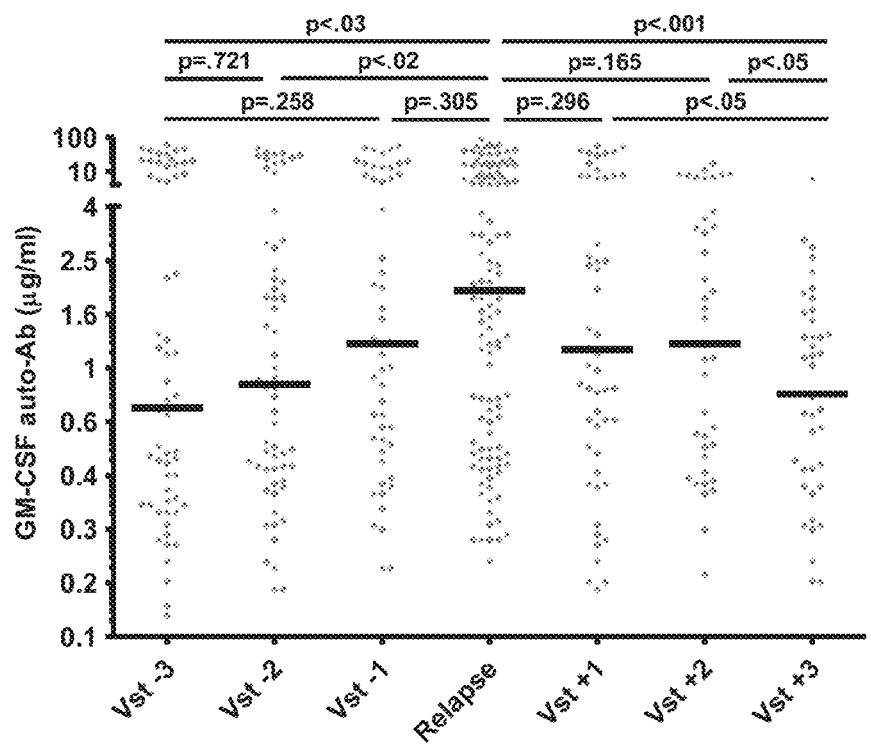

Time course analysis of GM-CSF Ab in patients with IBD and disease relapse showed an increase of neutralizing antibody concentrations starting up to 6 months before clinical relapse. See FIG. 1B. More specifically, GM-CSF Ab concentrations were at low levels 9 months before relapse and the levels increased steadily until the visit 6 months before relapse. GM-CSF Ab levels were even higher within 3 months before relapse and reached a peak during relapse. After relapse, GM-CSF Ab levels decreased within 2 to 6 months. In the further course, GM-CSF Ab levels decrease to baseline levels 9 months after relapse. Table 3 and Table 4 summarize serum GM-CSF Ab levels at different time points before, during and after relapse of IBD in CD patients and in UC patients, respectively.

TABLE 3

| | | Serum GM-CSF Ab levels | | | |
|---|---|---|---|---|---|
| Time interval in CD patients | | Median (µg/mL) | Range (µg/mL) | n | P |
| Before relapse | 7 to 9 months | 2.9 | 0.1-63 | 22 | <.01 |
| | 4 to 6 months | 12.8 | 3-47 | 11 | <.0001 |
| | 2 to 3 months | 16.0 | 2-57 | 6 | <.0005 |
| During relapse | | 21.5 | 0.2-576 | 54 | <.0001 |
| After relapse | 2 to 3 months | 8.0 | 0.2-528 | 9 | <.05 |
| | 4 to 6 months | 4.7 | 0.5-51 | 16 | <.0001 |
| | 7 to 9 months | 2.1 | 1-33 | 10 | <.0001 |

TABLE 4

| | | Serum GM-CSF Ab levels | | | |
|---|---|---|---|---|---|
| Time interval in UC patients | | Median (µg/mL) | Range (µg/mL) | n | P |
| Before relapse | 7 to 9 months | 0.42 | 0.1-8 | 38 | =.689 |
| | 4 to 6 months | 0.52 | 0.2-25 | 52 | <.05 |
| | 2 to 3 months | 0.67 | 0.1-21 | 47 | <.01 |
| During relapse | | 21.5 | 0.79 | 0.2-38 | 64 |
| After relapse | 2 to 3 months | 0.69 | 0.2-34 | 35 | <.05 |
| | 4 to 6 months | 0.64 | 0.2-30 | 36 | <.01 |
| | 7 to 9 months | 0.60 | 0.2-8 | 31 | =.104 |

Correlation of Serum GM-CSF Ab with Disease Location and Behavior in CD

Figure 1C:
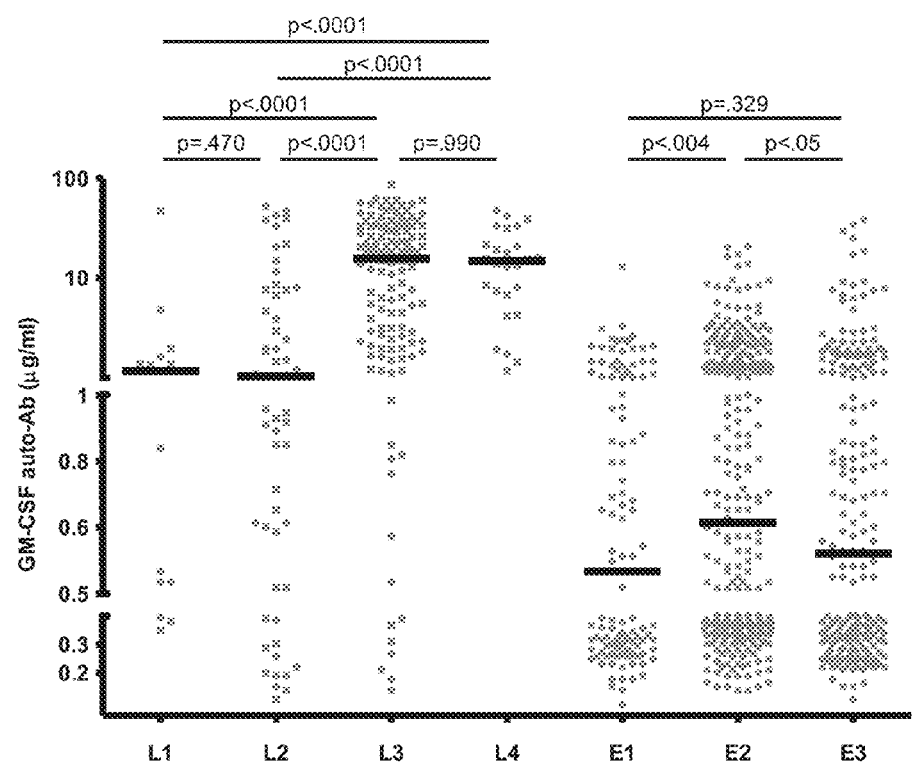

GM-CSF Ab were significantly higher in patients with CD and ileo-colonic disease (15.7 µg/mL; 0.2-88 µg/mL; n=128) as well as concomitant upper gastrointestinal disease (14.7 µg/mL; 1.2-48 µg/mL; n=26) than in those who had isolated ileal disease (1.2 µg/mL; 0.4-47 µg/mL; n=15; P<0.0001) or colonic disease (1.0 µg/mL; 0.1-576 µg/mL; n=60; P<0.0001). See FIG. 1C. Serum levels of GM-CSF Ab did not significantly differ with respect to stricturing and/or penetrating disease behavior of CD (data not shown).

Correlation of Serum GM-CSF Ab with Extent and Severity of UC

Levels of GM-CSF Ab were significantly higher in patients with moderate/severe disease (0.67 µg/mL; 0.1-38 µg/mL; n=241; P<0.0004) and mild disease (0.70 µg/mL; 0.1-8 µg/mL; n=145; P<0.05) than in those patients with UC who had no signs of disease activity (0.49 µg/mL; 0.02-14 µg/mL; n=228). Furthermore, GM-CSF Ab were highest in patients with left-sided (distal) ulcerative colitis (0.64 µg/mL; 0.1-21 µg/mL; n=295) compared with those with ulcerative proctitis (0.54 µg/mL; 0.1-13 µg/mL; n=113; P<0.004) and those with pancolitis (0.58 µg/mL; 0.02-38 µg/mL; n=206; P<0.05). See FIG. 1C.

Serum GM-CSF Ab in Patients with IBD in Stable Remission

Figure 1D:
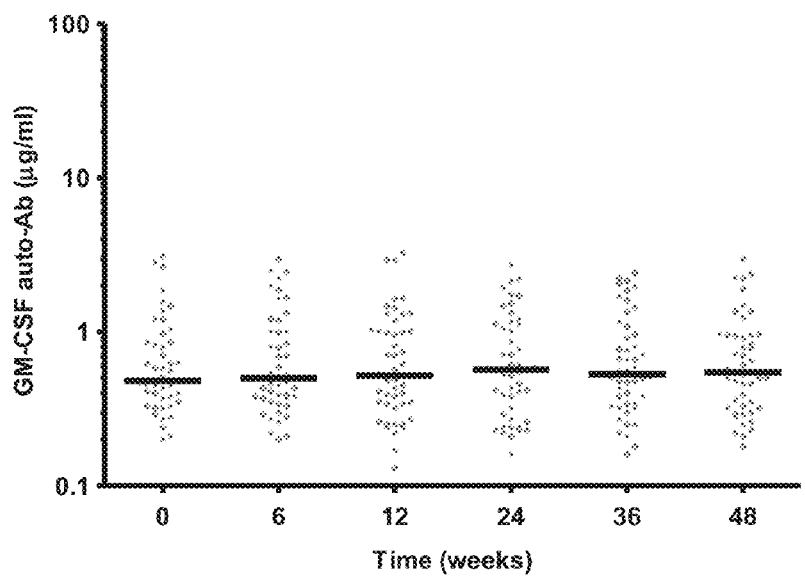

GM-CSF Ab levels in serum samples (n=290) of patients with IBD who had no clinical disease relapse during the study follow-up showed a low intra-individual variation (Δ0.4 µg/mL; 0.06-1.62 µg/mL). See FIG. 1D. Moreover, GM-CSF Ab levels were below the cut-point where GM-CSF Ab start to inhibit neutrophil anti-bacterial function (<5 µg/mL) in these patients. Uchida K, et al., Blood 2009; 113:2547-56. Accordingly, GM-CSF Ab levels were significantly lower in serum samples of patients without medication (0.6 µg/mL; 0.02-43 µg/mL; n=599) compared with GM-CSF Ab levels in serum samples of IBD patients who were treated with oral corticosteroids (2.0 µg/mL; 0.1-576 µg/mL; n=92; P<0.0001), 5-aminosalicylates (1.7 µg/mL; 0.2-88 µg/mL; n=78; P<0.0001), azathioprine (6.3 µg/mL; 0.2-63 µg/mL; n=81; P<0.0001), anti-tumor necrosis factor alpha (TNFα) agents (8.8 µg/mL; 0.4-576 µg/mL; n=131; P<0.0001), and/or methotrexate (1.8 µg/mL; 0.2-42 µg/mL; n=19; P<0.03).

Association of Serum GM-CSF Ab with Disease Activity Indices and Inflammatory Markers A significant correlation was found between GM-CSF Ab and fecal calprotectin. GM-CSF Ab were not correlated with clinical disease activity scores, fecal S100A12, C-reactive protein, erythrocyte sedimentation rate, white blood cell counts, hemoglobin, erythrocyte counts, platelet count, or hematocrit. Table 5 summarizes levels of correlation between serum GM-CSF auto-antibodies, disease activity, and inflammatory markers.

TABLE 5

| Inflammatory markers | Number of pairs (n) | Spearman's Correlation (r) | 95% Confidence Interval | P |
|---|---|---|---|---|
| Fecal S100A8/A9 | 306 | 0.203 | 0.089 to 0.311 | <0.0005 |
| Fecal S100A12 | 610 | 0.056 | −0.026 to 0.137 | 0.168 |
| CDAI | 166 | 0.132 | −0.025 to 0.283 | 0.090 |
| PCDAI | 67 | 0.081 | −0.170 to 0.321 | 0.516 |
| UCAI | 604 | 0.024 | −0.058 to 0.106 | 0.555 |
| PUCAI | 23 | −0.258 | −0.614 to 0.185 | 0.234 |
| CRP | 781 | −0.005 | −0.077 to 0.067 | 0.888 |
| ESR | 565 | −0.024 | −0.108 to 0.062 | 0.577 |
| White blood cells | 772 | −0.059 | −0.131 to 0.014 | 0.103 |
| Platelets | 772 | 0.072 | −0.002 to 0.142 | 0.051 |
| Hemoglobin | 772 | −0.011 | −0.083 to 0.062 | 0.766 |
| Red blood cells | 226 | −0.061 | −0.193 to 0.074 | 0.365 |
| Hematocrit | 241 | −0.018 | −0.147 to 0.113 | 0.786 |

Accuracy of Serum GM-CSF Ab in Predicting Clinical Relapse

Figure 2A:
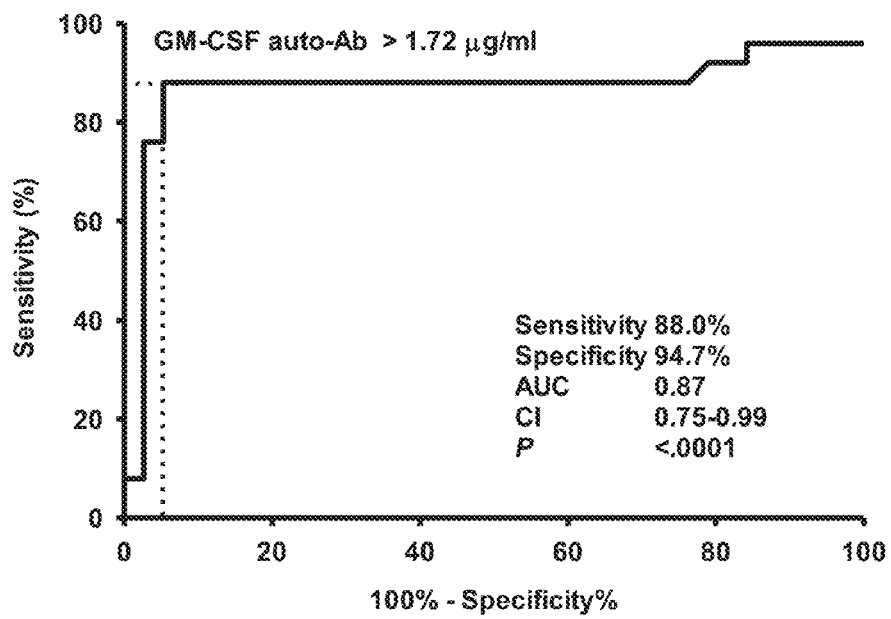
FIGS. 2A-2D relate to the accuracy of serum GM-CSF Ab in predicting clinical relapse.
Figure 2B:
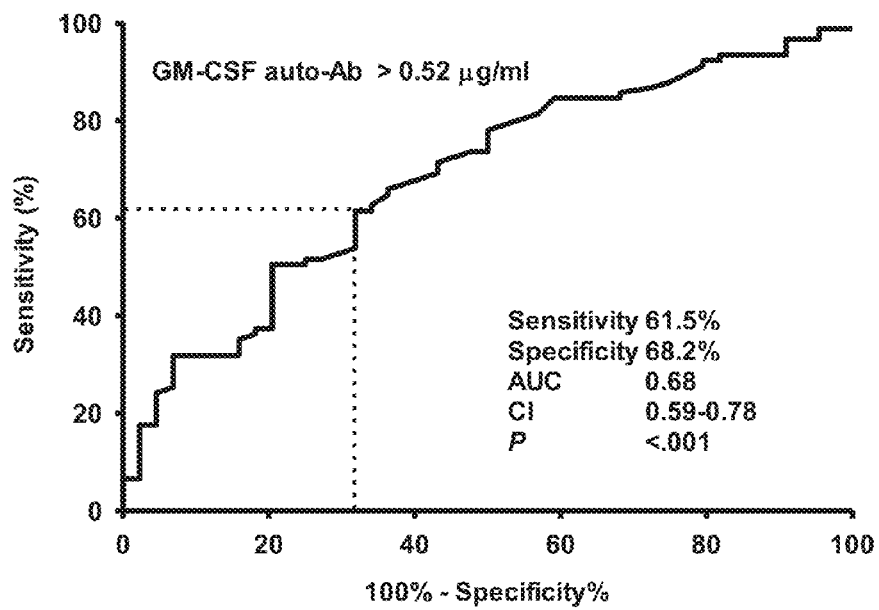
Figure 2C:
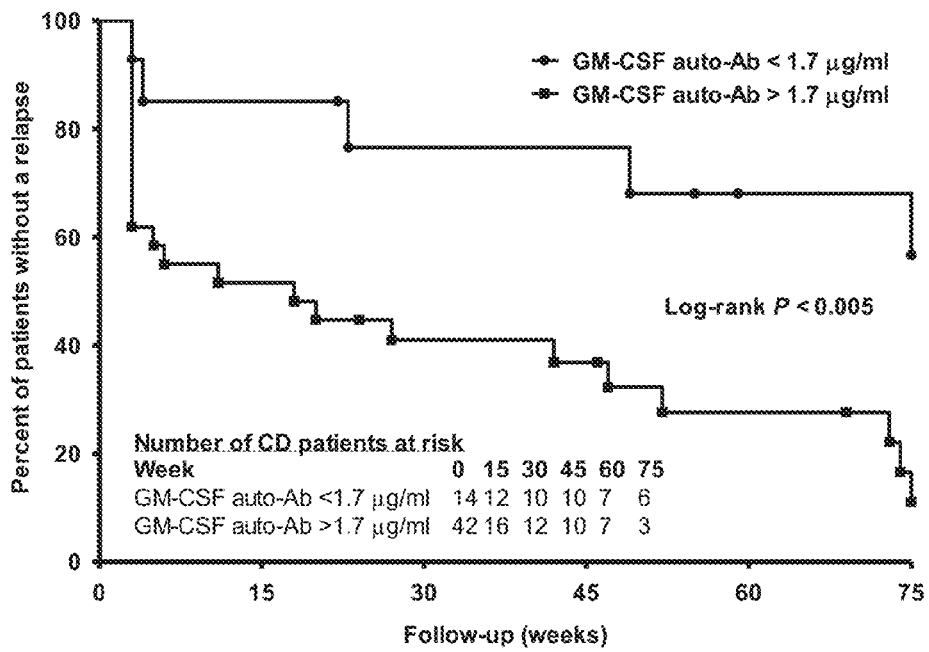
Figure 2D:
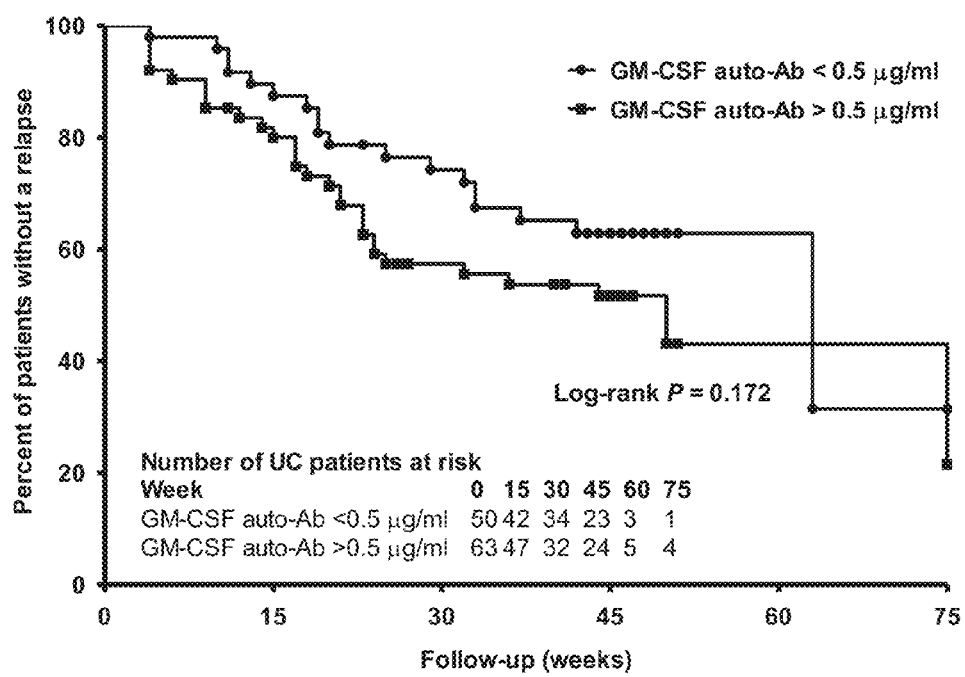

GM-CSF Ab concentrations of patients who had a relapse during follow-up were higher at inclusion into the study (1.7 μg/mL; 0.1-88 μg/mL; n=81) than in those who were continuously in remission (0.7 μg/mL; 0.2-61 μg/mL; n=87, P<0.05). ROC curve analyses were performed to analyze the sensitivity and specificity of GM-CSF Ab in differentiating patients with IBD with relapse from those in remission at 2 to 6 month before the relapse becomes clinically apparent. See FIGS. 2A-2D. In CD patients, a GM-CSF Ab concentration of about 1.7 μg/mL was more accurate in predicting clinical relapse; a ROC curve analysis provided a sensitivity=88.0%, specificity=94.7%, AUC=0.87, confidence interval (CI)=0.75-0.99, P<0.0001. See FIG. 2A. In UC patients, a GM-CSF Ab concentration of 0.5 μg/mL was more accurate in predicting clinical relapse; a ROC curve analysis provided a sensitivity=61.5%, specificity=68.2%, AUC=0.68, confidence interval (CI)=0.59-0.78, P<0.001. See FIG. 2B.

Indeed, the percentage of patients with IBD relapsing out of a status of disease remission during follow-up (CD, n=37; UC, n=53) was higher in patients having high GM-CSF Ab concentrations at the time of study enrollment in disease remission compared with those with low levels of GM-CSF Ab. A baseline GM-CSF Ab level of >1.7 μg/mL was significantly associated with clinical relapse of CD within 18 months. See FIG. 2C. In contrast, the difference in the proportion of patients with UC who relapsed over a 1.5-year period was not statistically significant when GM-CSF Ab concentrations (< or >0.5 μg/ml) were considered. See FIG. 2D. Table 6 and Table 7 summarize the number of patients at risk over time for particular GM-CSF Ab levels in CD and UC patients, respectively.

TABLE 6

| | Number of CD patients at risk | |
|---|---|---|
| Time (weeks) | Patient's GM-CSF Ab level at time of inclusion into study <1.7 μg/ml | Patient's GM-CSF Ab level at time of inclusion into study >1.7 μg/ml |
| 0 | 14 | 42 |
| 15 | 12 | 16 |
| 30 | 10 | 12 |
| 45 | 10 | 10 |
| 60 | 7 | 7 |
| 75 | 6 | 3 |

Log-rank P < 0.005

TABLE 7

| | Number of UC patients at risk | |
|---|---|---|
| Time (weeks) | Patient's GM-CSF Ab level at time of inclusion into study <0.5 μg/ml | Patient's GM-CSF Ab level at time of inclusion into study >0.5 μg/ml |
| 0 | 50 | 63 |
| 15 | 42 | 47 |
| 30 | 34 | 32 |
| 45 | 23 | 24 |
| 60 | 3 | 5 |
| 75 | 1 | 4 |

Log-rank P < 0.172

The study described herein examined whether serum GM-CSF Ab is a suitable marker for the confirmation of stable remission or the prediction of relapses of IBD during long-term follow-up. Serum GM-CSF Ab levels were found to be significantly elevated in patients with active CD or active UC compared with those with inactive IBD, and serum GM-CSF Ab titers correlated significantly with concentrations of fecal calprotectin (S100A8/A9).

Two previous cross-sectional studies on the role of GM-CSF Ab in IBD found no differences of serum GM-CSF Ab in subjects with inactive vs. active disease, or the authors did not assess the direct impact of GM-CSF Ab titers on disease activity (Han X, et al. Gastroenterology 2009; 136:1261-71, e1-3; and Gathungu G, et al. Granulocyte-macrophage colony-stimulating factor auto-antibodies: a marker of aggressive crohn's disease. Inflamm Bowel Dis 2013). These studies did not examine the relationship between serum GM-CSF Ab and disease activity within subjects longitudinally. In the study described herein which uses a longitudinal prospective design it is shown that GM-CSF Ab levels increase starting up to 6 months before clinical relapse; peak during relapse; and decline steadily during 9 months after relapse to baseline levels. Furthermore, serum GM-CSF Ab titers in patients with IBD in stable remission were found to be low and showed no relevant fluctuation as seen in patients with disease relapse.

The association of GM-CSF Ab levels with CD location and behavior, UC extent and severity were also examined. GM-CSF Ab titers were significantly higher in patients with ileo-colonic CD or concomitant upper gastrointestinal disease and in patients with left-sided (distal) ulcerative colitis. GM-CSF Ab levels did not differ as regards CD behavior or severity of active UC. Previous studies have shown that elevated GM-CSF level are significantly associated with ileal or ileo-colonic location of CD and stricturing or penetrating disease behavior (Han X, et al. Gastroenterology 2009; 136:1261-71, e1-3; and Gathungu G, et al. Granulocyte-macrophage colony-stimulating factor auto-antibodies: a marker of aggressive crohn's disease. Inflamm Bowel Dis 2013). However, the proportion of patients with CD and stricturing/penetrating disease was significantly higher in these prior studies (35-58%) compared to the study described herein (16%) and the association was not observed in subjects with colon-only disease.

Similar to previous studies, the GM-CSF Ab expression levels were confirmed to be elevated in CD compared to GM-CSF Ab expression levels in UC. The reason for the different result for GM-CSF Ab expression in CD and UC is not clear. However, both free GM-CSF and GM-CSF Ab have been shown to be produced by the affected tissue in ileal surgical specimens of patients with CD, and GM-CSF Ab were increased markedly in lamina propria mononuclear cells isolated from the stricture, suggesting a specific local tissue response. These data are consistent with the hypothesis that prolonged exposure to the cognate cytokine, in this case GM-CSF, leads to loss of T cell tolerance, and expansion of an existing pool of B cells producing GM-CSF autoantibodies (Watanabe M, et al. Cytokine Growth Factor Rev 2010; 21:263-73).

Biomarkers could be useful in selecting a need for invasive investigations, and in monitoring the disease course of patients with IBD. Fecal markers are a non-invasive way of objectively measuring intestinal inflammation and disease activity. A number of fecal markers have been evaluated for their ability to differentiate and monitor IBD disease activity (Foell D, et al. Gut 2009; 58:859-68; and Judd T A, et al. J Gastroenterol Hepatol 2011; 26:1493-9). Two members of the S100 family of calcium-binding proteins (calprotectin and S100A12) are amongst the most promising disease-specific markers, which have the potential to advance diagnostic and disease monitoring practices. However, the capacity of fecal S100 proteins in predicting relapse of quiescent IBD is not ideal and shows a sensitivity of 70% (S100A12) to 78% (calprotectin) and a specificity of 73% (calprotectin) to 83% (S100A12). Furthermore, evidence suggests that fecal S100 proteins are a stronger predictor of relapse in UC than in CD.

Interestingly, it has recently been shown that smokers with ileal CD have significantly lower GM-CSF Ab concentrations and that elevated GM-CSF Ab (≥5 µg/ml) were associated with significantly higher odds of having ileal disease location among non-smokers (Gathungu G, et al. Granulocyte-macrophage colony-stimulating factor auto-antibodies: a marker of aggressive crohn's disease. Inflamm Bowel Dis 2013). However, in the study described herein, no interaction of smoking status with CD location or GM-CSF Ab titers was found (data not shown). This may be caused by differences in the smoking status and the number of patients with ileal CD. The study of Gathungu et al. included 477 patients with CD, of whom 35% had ileal disease and 42% were current smokers or ex-smokers; whereas the study described herein included 61 patients with CD, of whom only 11% had ileal disease and only 6% were current smokers or ex-smokers. Furthermore, the effect of smoking on GM-CSF Ab expression in the study by Gathungu et al. did not reach significance in their second cohort and in a subset of CD patients with colon-only location.

Example 2—Measuring of Anti-GM-CSF Levels

GM-CSF participates in the growth and differentiation of myeloid and monocyte lineage cells. Pulmonary alveolar proteinosis (PAP) is a rare lung disorder characterized by the excessive accumulation of surfactant lipids and proteins in alveoli, resulting in impaired gas exchange and respiratory insufficiency. Clinically, PAP is divided into congenital, secondary, and idiopathic forms, with the latter comprising more than 90% of the cases. GM-CSF exerts its role over surfactant homeostasis by acting locally in the lung and stimulating alveolar macrophage terminal differentiation. An abnormality in or lack of sufficient GM-CSF signaling may cause impaired clearance of surfactant lipids and surfactant proteins by alveolar macrophage. This deficit could be overcome by the addition of excess GM-CSF. An autoantibody has a neutralizing effect on the level of GM-CSF resulting in impaired bioactivity. Autoantibodies directed at GM-CSF occur at high levels in the sera and lungs of patients with idiopathic PAP, but not in those with other lung diseases. High autoantibody levels are sensitive and specific for the diagnosis of idiopathic PAP. Thus, detecting autoantibodies by methods such as an Enzyme-linked Immunosorbent Assay (ELISA) has good predictive value for idiopathic PAP and suggests the clinical usefulness of this assay for the diagnosis of idiopathic PAP.

An ELISA for anti-GM-CSF utilizes a human recombinant GM-CSF antigen as a capture protein to coat the wells of a microtiter plate. The serum of the patient or healthy individual is appropriately diluted and added to the wells after blocking and washing. Next, a goat anti-human IgG labeled with horseradish peroxidase is used to detect the antigen-antibody complex attached to the well. The wells are washed once more and a substrate solution is added. Hydrolysis of the substrate by peroxidase produces a color change. The reaction is stopped by adding an acid stop solution, and the intensity of the solution is proportional to the antibody concentration in the test sample. The following is an example ELISA protocol.

Prepare multiwell plate: coat plate with 50 µl of 1 µg/ml recombinant human GM-CSF (rhGM-CSF) in PBS. Cover ELISA plate with ELISA sticker, and incubate overnight at 4° C. Remove plate from 4° C., discard the reagent, and wash plate with wash buffer (PBS.0.1% Tween 20), 5 times using BioRad Immuno-wash™ protocol "wash ×5". Add 100 µL Blocking Buffer (PBS/0.1% Tween 20/1.5% dry milk) to each well using multichannel pipette and clean reagent troughs. Cover plate with ELISA sticker, and incubate at room temperature for 1 hour on bench top. Discard the reagent and remove the blocking buffer solution completely by blotting the plate onto paper towel.

Dilute serum with Blocking buffer:PAP patients: 1:3000, 1:6000, and 1:12000; Healthy patients or Patients with other disease: 1:100; BAL fluid: 1:10 and 1:100. Add 50 µL appropriately diluted samples, standards, and controls to wells. Cover with ELISA sicker, and incubate at room temperature for 40 minutes on bench top.

Wash plate 5 times with wash buffer using BioRad Immuno-wash™ protocol "wash ×5". A washing step consists of the following procedures: dispense 450 µl of wash buffer into each well and aspirate wash buffer completely. Add 50 µL of 10 mM ammonium acetate pH 5.0. Cover with ELISA sticker and incubate at room temperature for 15 minutes. Discard the reagent and wash once with wash buffer using BioRad Immuno-wash™ protocol "wash ×1"

Add 50 µL of HRP-goat anti-human IgG F(ab')2 diluted 1:3000 in 0.1% goat serum in PBS/0.1% Tween 20. (e.g. 2 µl conjugate into 6 mL buffer=1:3000). Incubate at room temperature for 30 minutes.

Wash plate four times with wash buffer using BioRad Immuno-wash™ protocol "wash ×4" Add 50 µl TMB substrate solution. Cover ELISA plate with plate sticker. Wrap the plate in foil immediately after adding TMB. Incubate for 10 minutes absent from light. After 10 minutes, check that the standards of highest concentration and the positive control have turned to a blue color. Stop color development with 50 µL of 1 N sulfuric acid. At this step the blue color solution of positive wells turns to yellow. Remove air bubbles on the surface of each well that interfere with plate readers absorbance reading using an new/unused 200 µL pipette tip for each well. Read absorbance at 450 nm wavelength with microplate reader. Calculate concentrations by generating a standard curve using controls.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of determining and treating an increased relapse risk for a subject having inflammatory bowel disease (IBD) in clinical remission, comprising:
   measuring an increased level of an anti-GM-CSF antibody in a serum sample from said subject compared to the level of the anti-GM-CSF antibody in a serum sample obtained from said subject at a prior time, thereby determining an increased IBD relapse risk within 2 months for said subject; and
   administering a treatment to the subject for said increased IBD relapse risk, wherein the treatment is selected from a surgery effective to treat the increased IBD relapse risk, and an effective amount of a therapeutic agent to treat the increased IBD relapse risk, the therapeutic agent selected from the group consisting of a corticosteroid, a 5-aminosalicylate, azathioprine, 6-mercaptopurine, a tumor necrosis factor (TNF) inhibitor, and methotrexate, wherein the treatment is modified from an IBD therapy administered to the subject, or alternative to an IBD therapy administered to the subject.

2. The method of claim 1, wherein said measuring comprises contacting the serum sample with an antibody or antigen-binding fragment thereof.

3. The method of claim 1, wherein the treatment comprises inducing remission.

4. The method of claim 1, wherein the IBD is selected from the group consisting CD and UC.

5. The method of claim 4, wherein the CD is selected from the group consisting of illeal CD, colonic CD, illeo-colic CD, and upper gastrointestinal CD.

6. The method of claim 4, wherein the UC is selected from the group consisting of ulcerative proctitis, left-sided colitis, and pancolitis.

7. The method of claim 1, wherein the sample is ex vivo.

8. The method of claim 1, further comprising measuring the level of fecal S100A8/A9 in a fecal sample from said subject.

9. A method of determining and treating a relapse risk for a subject having inflammatory bowel disease (IBD) in clinical remission, comprising:
   measuring the level of an anti-GM-CSF antibody in a serum sample from said subject;
   detecting an increased level of an anti-GM-CSF antibody in a second serum sample obtained from the subject compared to the level of the anti-GM-CSF antibody in a first serum sample obtained from said subject at a prior time is indicative of an increased IBD relapse risk within 2 months, thereby determining the IBD relapse risk for said subject;
   selecting a treatment for said IBD relapse risk; and
   administering a treatment to the subject for an increased IBD relapse risk, wherein the treatment is selected from a surgery effective to treat the increased IBD relapse risk and an effective amount of a therapeutic agent to treat the increased IBD relapse risk, the therapeutic agent selected from the group consisting of a corticosteroid, a 5-aminosalicylate, azathioprine, 6-mercaptopurine, a tumor necrosis factor (TNF) inhibitor inhibitor, and methotrexate, wherein the treatment is modified from an IBD therapy administered to the subject, or alternative to an IBD therapy administered to the subject.

10. The method of claim 9 comprising:
    detecting an increased level of fecal S100A8/A9 in a fecal sample obtained from the subject compared to the level of fecal S100A8/A9 in a fecal sample obtained from said subject at a prior time.

11. The method of claim 9, wherein the first serum sample is obtained at least 8 weeks previous to the second serum sample.

12. The method of claim 9, wherein the concentration of anti-GM-CSF antibody in the second serum sample is greater than 1.7 µg/mL.

13. The method of claim 9, wherein the TNF inhibitor is selected from the group consisting of infliximab, adalimumab, and natalizumab.

14. A method of treating a subject having inflammatory bowel disease (IBD) in clinical remission, comprising:
    measuring a concentration of anti-GM-CSF antibodies in a serum sample from a subject;
    determining if the measured concentration is greater than 1.7 µg/mL, wherein the subject is predicted to have a risk of IBD relapse within 2 months; and
    administering a treatment to the subject for increased IBD relapse risk if the measured concentration of anti-GM-CSF antibodies is determined to be greater than 1.7 µg/mL, wherein the treatment is selected from a surgery effective to treat the increased IBD relapse risk and an effective amount of a therapeutic agent to treat the increased IBD relapse risk, the therapeutic agent selected from the group consisting of a corticosteroid, a 5-aminosalicylate, azathioprine, 6-mercaptopurine, a tumor necrosis factor (TNF) inhibitor, methotrexate, wherein the treatment is modified from an IBD therapy administered to the subject, or alternative to an IBD therapy administered to the subject.

15. The method of claim 14 comprising:
    detecting an increased level of fecal S100A8/A9 in a second fecal sample obtained from the subject compared to the level of fecal S100A8/A9 in a first fecal sample obtained from said subject at a prior time.

16. The method of claim 15, wherein the first fecal sample is obtained at least 8 weeks previous to the second fecal sample.

17. The method of claim 14, wherein the treatment is administration of a tumor necrosis factor (TNF) inhibitor selected from the group consisting of infliximab, adalimumab, and natalizumab.

18. The method of claim 1, wherein the treatment is administration of a tumor necrosis factor (TNF) inhibitor selected from the group consisting of infliximab, adalimumab, and natalizumab.

* * * * *

UNITED STATES PATENT AND TRADEMARK OFFICE
CERTIFICATE OF CORRECTION

| | | |
|---|---|---|
| PATENT NO. | : 9,995,752 B2 | Page 1 of 1 |
| APPLICATION NO. | : 14/890257 | |
| DATED | : June 12, 2018 | |
| INVENTOR(S) | : Lee A. Denson | |

It is certified that error appears in the above-identified patent and that said Letters Patent is hereby corrected as shown below:

On the Title Page

Column 1, (Notice) at Line 3, After "0 days." delete "days.".

Item (57), (Abstract) at Line 3, Change "n" to --in--.

In the Specification

In Column 2 at Line 65, Change "illeo-colic" to --ileo-colic--.

In Column 5 at Line 57, Change "illeo-colic" to --ileo-colic--.

In Column 7 at Line 29, Change "methods" to --methods.--.

In Column 9 at Line 21, Change "anti-GMCSF" to --anti-GM-CSF--.

In Column 9 at Line 21-22, Change "anti-GMCSF" to --anti-GM-CSF--.

In Column 16 at Line 43, Change ""wash ×1"" to --"wash ×1".--.

In the Claims

In Column 17 at Line 63, In Claim 5, change "illeo-colic" to --ileo-colic--.

In Column 18 at Line 26-27, In Claim 9, change "inhibitor inhibitor," to --inhibitor,--.

Signed and Sealed this
Eleventh Day of September, 2018

Andrei Iancu
*Director of the United States Patent and Trademark Office*